(12) United States Patent
Brown et al.

(10) Patent No.: US 8,551,533 B2
(45) Date of Patent: Oct. 8, 2013

(54) ADJUVANT COMPOSITION AND AGROCHEMICAL FORMULATION CONTAINING SAME

(75) Inventors: William L Brown, Pleasantville, NY (US); Kalman Koczo, Suffern, NY (US); George A Policello, Ossining, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 107 days.

(21) Appl. No.: 13/103,630

(22) Filed: May 9, 2011

(65) Prior Publication Data
US 2012/0289402 A1 Nov. 15, 2012

(51) Int. Cl.
| | | |
|---|---|---|
| A01N 59/16 | (2006.01) | |
| A01N 59/06 | (2006.01) | |
| A01N 59/02 | (2006.01) | |
| A01N 25/00 | (2006.01) | |
| A01N 59/00 | (2006.01) | |
| A01N 55/02 | (2006.01) | |
| A61K 33/06 | (2006.01) | |
| A61K 33/08 | (2006.01) | |
| A61K 33/04 | (2006.01) | |

(52) U.S. Cl.
USPC ......... 424/641; 424/682; 424/684; 424/688; 424/691; 424/703; 504/116.1; 504/119; 504/120; 504/121; 504/126

(58) Field of Classification Search
None
See application file for complete search history.

(56) References Cited

U.S. PATENT DOCUMENTS

| | | | |
|---|---|---|---|
| 3,383,327 A | 5/1968 | Sullivan | |
| 3,455,839 A | 7/1969 | Rauner | |
| 3,746,653 A | 7/1973 | Churchfield | |
| 3,865,544 A | 2/1975 | Keil | |
| 4,075,118 A | 2/1978 | Gault et al. | |
| 4,370,358 A | 1/1983 | Hayes et al. | |
| 4,524,002 A | 6/1985 | Hashem | |
| 4,961,877 A | 10/1990 | Shimizu et al. | |
| 5,082,590 A | 1/1992 | Araud | |
| 5,341,932 A | 8/1994 | Chen et al. | |
| 5,464,807 A | 11/1995 | Claude et al. | |
| 5,556,577 A | 9/1996 | Gomes et al. | |
| 5,652,197 A | 7/1997 | Claude et al. | |
| 5,693,256 A | 12/1997 | Sawicki et al. | |
| 5,756,441 A | 5/1998 | Thomas et al. | |
| 5,968,872 A | 10/1999 | Policello et al. | |
| 6,107,249 A | 8/2000 | Wikeley | |
| 6,180,117 B1 | 1/2001 | Berthiaume et al. | |
| 6,207,617 B1 | 3/2001 | Gillespie | |
| 6,207,722 B1 | 3/2001 | Juen et al. | |
| 6,500,782 B1 | 12/2002 | Kassebaum | |
| 6,746,988 B2 | 6/2004 | Hopkinson et al. | |
| 7,008,904 B2 | 3/2006 | Crockett et al. | |
| 7,316,990 B2 | 1/2008 | Tank et al. | |
| 7,678,835 B2 | 3/2010 | Koczo et al. | |
| 7,763,567 B2 | 7/2010 | Perry et al. | |
| 7,842,647 B2 | 11/2010 | Long | |
| 7,872,053 B2 | 1/2011 | Wagner et al. | |
| 7,879,918 B2 | 2/2011 | Koczo et al. | |
| 2005/0249689 A1 | 11/2005 | Kuo et al. | |
| 2007/0112078 A1 | 5/2007 | Procter et al. | |
| 2008/0293606 A1 | 11/2008 | Rautschek et al. | |

FOREIGN PATENT DOCUMENTS

| | | | |
|---|---|---|---|
| CN | 101913942 | * | 12/2010 |
| CN | 101953346 | * | 1/2011 |
| EP | 0163541 A2 | | 12/1985 |
| EP | 0254499 A2 | | 1/1988 |
| EP | 0663225 A1 | | 7/1995 |
| EP | 0220902 B1 | | 4/1998 |
| EP | 1075864 A2 | | 2/2001 |
| EP | 1167456 A1 | | 1/2002 |
| WO | 2005/058454 A1 | | 6/2005 |
| WO | 2008127661 A1 | | 10/2008 |
| WO | 2010039575 A1 | | 4/2010 |
| WO | 2010/091044 A2 | | 8/2010 |
| WO | 2010/133249 A1 | | 11/2010 |

OTHER PUBLICATIONS

Momentive: "Silicone Specialities for Agricultural Applications," Jan. 30, 2009, pp. 1-4, XP55032886; Retrieved from the Internet: URL:http://www.momentiveperformancematerials.biz/momentiveInternetDoc/Internet/Static Files/ Documents/Marketing Bulletin/Ag Guide. pdf [retrieved on Jul. 17, 2012] Foam Control Agents; p. 2.

\* cited by examiner

*Primary Examiner* — Alton Pryor
(74) *Attorney, Agent, or Firm* — Dominick G. Vicari; Kenneth S. Wheelock

(57) ABSTRACT

An adjuvant composition is provided which comprises:
(a) at least one water-soluble electrolyte;
(b) at least one electrolyte-tolerant surfactant;
(c) antifoam component which is at least one mixture selected from the group consisting of (1) at least one branched silicone resin (i), at least one silicone fluid (ii), at least one particulate metal oxide (iii) and, optionally, at least one catalyst (iv) for catalyzing the condensation of siloxy groups, (2) the equilibration reaction product of mixture (1), and (3) mixture (1) in which at least a portion of particulate metal oxide (iii) is pre-hydrophobized;
(d) optionally, at least one additional bioinert material; and,
(e) water.

18 Claims, 1 Drawing Sheet

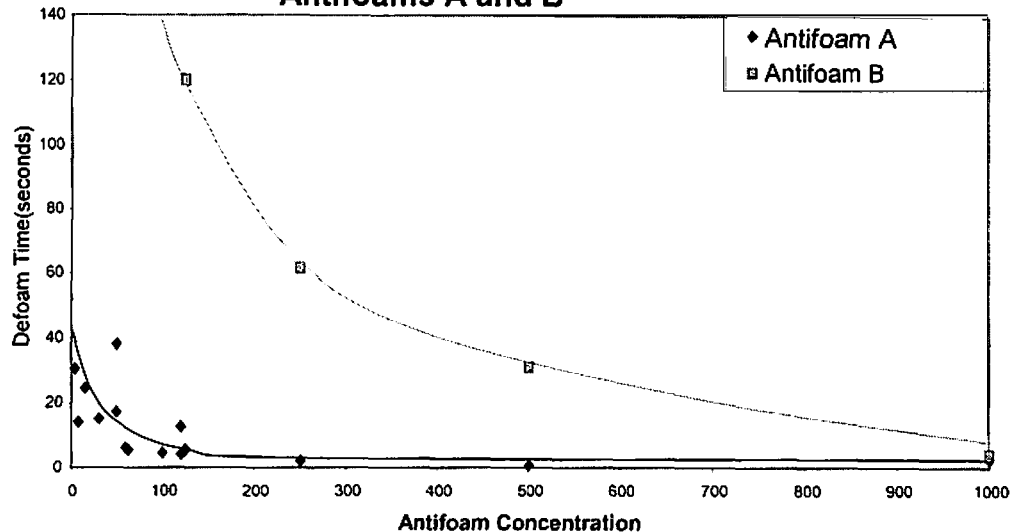
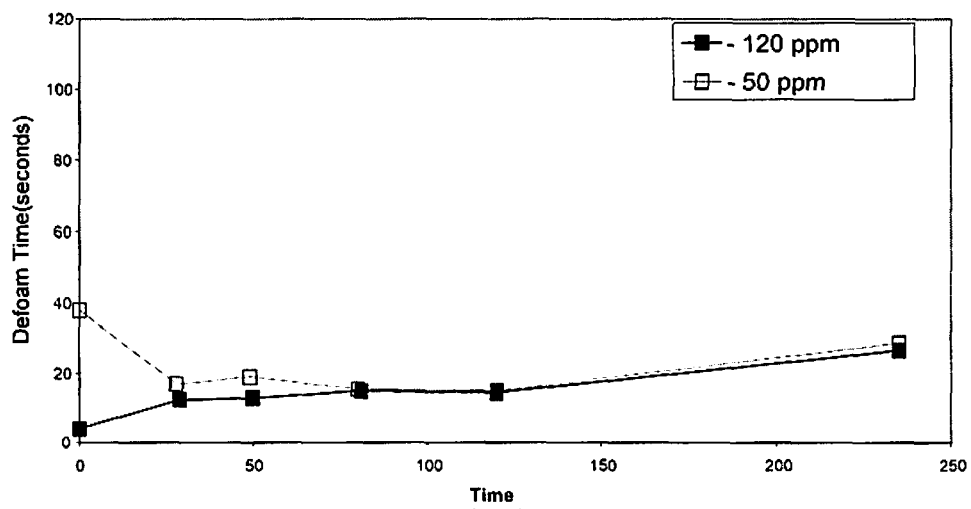

ADJUVANT COMPOSITION AND AGROCHEMICAL FORMULATION CONTAINING SAME

BACKGROUND OF THE INVENTION

This invention relates to adjuvant compositions particularly useful for the formulation of agrochemical actives such as pesticides.

Many adjuvant compositions intended for use in agrochemical formulations contain high levels of electrolytes (salts), particularly those electrolytes functioning as water conditioners, fertilizers or plant nutrients. When, in addition to high levels of electrolyte(s), such adjuvant compositions contain one or more electrolyte-tolerant surfactants, foaming is often a problem. It is therefore common practice to introduce an antifoam (defoamer) component in adjuvant compositions containing these surfactants in order to facilitate the preparation of application-ready agrochemical formulations containing the adjuvants and/or prevent problems from arising in connection with the application of the formulations in the field.

The antifoams used in conjunction with these high electrolyte products are usually silicone-based. However, known silicone-based antifoams are not without their drawbacks. Current silicone antifoams are commonly used in relatively high amounts in order to achieve an acceptable level of foam control, e.g., in an amount of at least 0.050 weight percent for many concentrated agrochemical formulations. Known silicone antifoams are prone to separation, especially during storage, leading to handling difficulties in the diluting/mixing operation, the field application of the final formulations and, potentially, the effectiveness of the latter.

BRIEF DESCRIPTION OF THE INVENTION

In accordance with the present invention, an adjuvant composition is provided which comprises:
(a) at least one water-soluble electrolyte;
(b) at least one electrolyte-tolerant surfactant;
(c) antifoam component which is at least one mixture selected from the group consisting of (1) at least one branched silicone resin (i), at least one silicone fluid (ii), at least one particulate metal oxide (iii) and, optionally, at least one catalyst (iv) for catalyzing the condensation of siloxy groups, (2) the equilibration reaction product of mixture (1), and (3) mixture (1) in which at least a portion of particulate metal oxide (iii) is pre-hydrophobized;
(d) optionally, at least one additional bioinert material; and,
(e) water.

Further in accordance with this invention, there is provided an agricultural formulation which comprises the adjuvant composition, supra, and
(f) at least one agrochemical.

The adjuvant composition of this invention incorporating the unique antifoam component (c) referred to above and described more fully hereinafter exhibits a level of stability and effectiveness markedly greater than adjuvant compositions that are identical in every respect to those herein except for containing known silicone-based antifoam components.

The superior stability of adjuvant compositions prepared in accordance with this invention can be achieved with levels of antifoam component that are as low as, and even significantly lower than, the lowest levels of known silicone-based antifoams, an advantageous attribute that translates into lower production costs for the adjuvant compositions herein.

The expression "water-soluble electrolyte" as used herein shall be understood to refer to any water-soluble material containing free ions that make the material electrically conductive. The expression "water-soluble electrolyte" therefore covers all acids, bases and salts, inorganic or organic, bioactive or bioinert, that in aqueous solution provide ionic species.

The expression "electrolyte-tolerant surfactant" herein refers to those surfactants that remain physically compatible in an aqueous composition containing a relatively high concentration of electrolyte (salt) in contrast to those surfactants that in an aqueous composition containing the same high concentration of the same electrolyte exhibit physical incompatibility, either immediately or soon after preparation or over time, or when exposed to destabilizing temperature conditions and/or other destabilizing factors, as manifested, e.g., by phase separation, formation of aggregates or agglomerates that interfere with handling, final product application and/or in a reduction of applied product effectiveness.

The term "agrochemical" as used herein shall be understood to refer to all bioactive compounds, biological materials including extracts, fractions and by-products thereof, living organisms including microorganisms, and the like, that are suitable for agricultural use such as pesticides, herbicides, fungicides, insecticides, nematocides, larvacides, mitocides, ovacides, plant growth regulators, seed treatment agents, etc. It shall be further understood that in the particular case of an agricultural formulation of the present invention where agrochemical (f) is also a water-soluble electrolyte and water-soluble electrolyte (a) of the adjuvant composition is also a bioactive compound, agrochemical (f) and electrolyte (a) cannot be satisfied by the same material.

As used in the specification and in the appended claims, the singular forms "a," "an," and "the" include the plural, and reference to a particular numerical value includes at least that particular value unless the context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about." It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

BRIEF DESCRIPTION OF THE DRAWINGS

FIG. 1 is a graph of experimental data comparing the performance of an adjuvant composition incorporating anti foam component A in accordance with the invention and the identical composition except for incorporating known silicone-based antifoam component B; and, FIG. 2 is a graph of experimental data comparing the long term stability and foam-controlling effectiveness of antifoam component A of the invention employed in the aforementioned adjuvant composition at two different levels of concentration therein.

DETAILED DESCRIPTION OF PREFERRED EMBODIMENTS

The adjuvant composition of this invention includes at least one water-soluble electrolyte (a); at least one electrolyte-tolerant surfactant (b); at least one antifoam component (c); optionally, at least one additional bioinert component (d); and, water (e). The agricultural formulation of this invention includes the foregoing adjuvant composition and at least one agrochemical (f).

Each of the aforementioned materials and representative embodiments thereof, representative embodiments of adjuvant compositions incorporating these materials and representative embodiments of agrochemical formulations containing such adjuvant compositions will now be described in detail.

Water-Soluble Electrolyte (a)

Water-soluble electrolyte (a) which can be incorporated in the adjuvant composition of this invention may, for example (and as a non limiting list of examples), comprise a cation or mixtures of cations which may include: aluminium, ammonium, antimony, barium, bismuth, cadmium, calcium, cesium, copper, iron, lithium, magnesium, nickel, potassium, rubidium, silver, sodium, strontium, zinc or zirconium; and an anion or mixtures of anions or polyatomic anions which may include: acetate, aluminum sulfate, aminechlorides, aminenitrates, aminesulfate, aminethionates, ammonium tartrate, azide, benzenesulfonate, benzoate, bicarbonate, bisulfite, borate(s), borohydride, borotartrate, borooxalate, bromate, bromide, butyrate, camphorate, carbonate, chlorate, chloride, chlorite, chromate, cinnamate, citrate, cyanate, cyanide, dichromate, disilicate, dithionate, ethylsulfate, ferricyanide, ferrocyanide, ferrocyanide, fluoride, fluoantimonate, fluoborate, fluoroacetate, fluorophosphates, fluorosulfonate, fluosilicate, formaldehyde-sulfoxylate, formate, furanacrylate, glycerophosphate, hydrogen carbonate, hydrogen sulfate, hydrogen sulfite, hydrogencyanide, hydrogenophosphate, hydrogensulfate, hydrosulfite, hydroxide, hydroxostannate, hypochlorite, hyponitrite, hypophosphite, iodate, iodide, isobutyrate, lactate, laureate, manganate, meta-aluminate, metaborate, metaperiodate, metasilicate, methionate, methylsulfate, mixed halides, molybdate, nitrate, nitrite, oleate, orthophosphate, orthophosphite, orthosilicate, oxalate, oxalatoferrate, oxide, oxides, perborate, perchlorate, perchlorate, permanganate, peroxide, peroxydisulfate, phenolsulfonate, phenoxide, phosphate, polybromides, polychlorides, polyfluorides, polyiodides, polysulfides, propionate, pyrosulfate, pyrosulfite, salicylate, sesqui-carbonate, silicate, silicate, sorbate, stannate, stearate, succinate, sulfamate, sulfanilate, sulfate, sulfide, sulfite, tartrate, thiocarbamate, thiocyanate, thiosulfate or valerate; either in their coordinated, anhydrous or hydrated forms.

Preferred water-soluble electrolytes (a) are those in which the cations are inorganic and/or those which are inorganic salts. Among the preferred water-soluble electrolytes (a) are known and conventional fertilizers and plant nutrients such as ammonium sulfate, ammonium chloride, ammonium nitrate, ammonium phosphate, urea ammonium nitrate (VAN), nitrophosphate, calcium nitrate, sodium nitrate, monocalcium phosphate monohydrate (triple superphosphate, or TSP), potassium chloride, potassium sulfate, potassium nitrate, potassium phosphate, calcium chloride, and the like. Of these, the ammonium salts, in particular, ammonium sulfate, ammonium chloride, ammonium nitrate, ammonium phosphate, urea ammonium nitrate and mixtures thereof, are especially advantageous water-soluble electrolytes (a) for incorporation in the adjuvant composition of this invention.

The total amount of electrolyte(s) (a) incorporated in the adjuvant composition of this invention can be at fairly high levels, e.g., those typical of fertilizer use, and can range, e.g., from 5 to 60, preferably from 10 to 50, and more preferably from 20 to 40, weight percent.

Electrolyte-Tolerant Surfactant (b)

Suitable electrolyte-tolerant surfactants (b) for incorporation in the adjuvant composition of this invention include alkyl polyglucosides (APGs), alkoxylated alkylamines (alkyletheramines), betaines, N-acyl sarcosinates, N-acyl glutamates, alkyl phosphate esters, alkylether phosphates, quaternary ammonium surfactants and their mixtures. Electrolyte-tolerant surfactant(s) (b) can be incorporated in the adjuvant composition of the invention over a wide range of amounts, e.g., from 1 to 30, and preferably from 2 to 20, weight percent thereof.

Alkyl polyglucosides which can be used in the adjuvant composition herein include those corresponding to the formula:

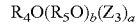

$$R_4O(R_5O)_b(Z_3)_a$$

wherein $R_4$ is a monovalent organic radical of from 6 to 30 carbon atoms; $R_5$ is a divalent alkylene radical of from 2 to 4 carbon atoms; $Z_3$ is a glucose residue of 5 or 6 carbon atoms; a is a number ranging from 1 to 6; and, b is a number ranging from 0 to 12. Preferred alkyl polyglucosides are those in which $R_4$ is a monovalent organic radical of from 8 to 10 carbon atoms; a has a value of from 1 to 3, e.g., 1.5 to 1.7; and, b is 0.

Some non-limiting examples of commercially available alkyl polyglucosides include, e.g., APG®, Agnique®, or Agrimul® surfactants from Cognis Corporation, Atlox surfactants from Uniqema, and surfactants from Akzo Nobel Surface Chemistry, LLC, such as:

1. Agnique PG 8105 Surfactant—an alkyl polyglucoside in which the alkyl group contains 8 to 10 carbon atoms and having an average degree of polymerization of 1.5.
2. Agnique PG 8166 Surfactant—an alkyl polyglucoside in which the alkyl group contains 8 to 16 carbon atoms and having an average degree of polymerization of 1.6.
3. Agnique PG 266 Surfactant—an alkyl polyglucoside in which the alkyl group contains 12 to 16 carbon atoms and having an average degree of polymerization of 1.6.
4. Agnique PG 9116 Surfactant—an alkyl polyglucoside in which the alkyl group contains 9 to 11 carbon atoms and having an average degree of polymerization of 1.6.
5. Agnique PG 264-U Surfactant—an alkyl polyglucoside in which the alkyl group contains 12 to 16 carbon atoms and having an average degree of polymerization of 1.4.
6. Agnique PG 8107 Surfactant—a $C_{8-16}$ alkyl polyglucoside in which the alkyl group contains 8 to 10 carbon atoms and having an average degree of polymerization of 1.7.

7. Agnique PG 266 Surfactant—a $C_{12-16}$ alkyl polyglucoside in which the alkyl group contains 12 to 16 carbon atoms and having an average degree of polymerization of 1.6.

8. AL 2575/AL 535 Surfactant—a $C_{8-11}$ alkyl polyglucoside in which the alkyl group contains 8 to 11 carbon atoms and having a HLB 12-13.

9. Akzo Nobel AG 6202, AG 6206, or AG 6210 surfactants which are 2 ethylhexyl branched C8, linear hexyl C6, and linear C8-C10 alkyl polyglucosides, respectively.

Among the useful alkoxylated alkylamine surfactants that can be utilized in the adjuvant composition of the invention are the polycondensates of from 1-20 moles of ethylene oxide with fatty amines of from 8 to 22 carbon atoms such as tallow amine, and the alkoxylated alkylamine surfactants described in U.S. Pat. No. 7,316,990, the entire contents of which are incorporated by reference herein.

Examples of useful betaines include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bix-(2-hydroxypropyl) carboxymethyl betaine, oleyl dimethyl gamma-carboxypropyl betaine, lauryl bix-(2-hydroxypropyl) alpha-carboxyethyl betaine, etc. The sulfobetaines may be represented by coco dimethyl sulfopropyl betaine, stearyl dimethyl sulfopropyl betaine, amido betaines amidosulfobetaines, and the like. The generally preferred betaines are those with long chain alkyl groups such as coco which is preferred. Betaines possessing amido groups are also preferred. The most preferred betaines are the cocoamido propyl or ethyl betaines.

Useful N-acyl sarcosinates and N-acyl glutamates include sodium lauroyl sarcosinate, sodium cocoyl sarcosinate, sodium myristoyl sarcosinate, ammonium lauroyl sarcosinate, sodium cocoyl glutamate, disodium cocoyl glutamate and sodium lauroyl glutamate, e.g., the Perlastan® series of sarcosinates and glutamates available from Struktol Company of America, Stow, Ohio.

Alkyl phosphate esters and alkylether phosphates that find use herein include the mixed mono- and diester phosphates such as those described in aforementioned U.S. Pat. No. 7,316,990.

Useful quaternary ammonium surfactants include those described in aforementioned U.S. Pat. No. 7,316,990.

Antifoam Component (c)

Antifoam component (c) in the adjuvant composition of the invention is provided as at least one of (1) a physical mixture of at least one branched silicone resin (i), at least one silicone fluid (ii), at least one particulate metal oxide (iii) and, optionally, at least one catalyst (iv) for catalyzing the condensation of siloxy groups, (2) the equilibration reaction product of mixture (1), and (3) mixture (1) in which at least a portion of particulate metal oxide is pre-hydrophobized.

Particularly preferred branched silicone resins (i) are those of the general formula:

wherein M is $SiO_{1/2}(R^1)_3$, T is $SiO_{3/2}R^2$, D is $SiO_{2/2}(R^3)_c$, Q is $SiO_{4/2}$, $R^1$, $R^2$ and $R^3$ each independently is a monovalent hydrocarbon radical of from 1 to 18 carbon atoms, a is greater than 0.1, b is 0 to 1000, c is 0 to 1,000 and d is 1-1000.

Particularly preferred branched silicone resins (i) are the MQ resins which are well known in the art. See, for example, U.S. Pat. Nos. 4,370,358 and 5,693,256 and US 2005/0249689, the entire contents of which are incorporated by reference herein.

The MQ resins can have any suitable M:Q ratio, and more preferably, an M:Q ratio within the range of from 0.1:1 to 1.5:1 or from 0.1:1 to 2:1. More preferably, the M:Q ratio is in the range of from 0.5:1 to 1.1:1. For example, in different embodiments, the M:Q ratio can preferably be 0.1:1, 0.2:1, 0.3:1, 0.4:1, 0.5:1, 0.6:1, 0.7:1, 0.8:1, 0.9:1, 1:1, 1.1:1, 1.2:1, 1.5:1, or 2:1. A particularly suitable MQ resin is commercially available under the trade name SR 1000 from Momentive Performance Materials Inc.

Silicone fluid (ii) is preferably a polydimethylsiloxane-containing (i.e., PDMS-containing) polymer. Silicone fluid (ii) can have any suitable viscosity, e.g., from 0.65 Centistokes (cSt) to 1,000,000 cSt, and more preferably from 0.65 Centistokes (cSt) to 100,000 cSt, and even more preferably, from 100 cSt to 20,000 cSt. The molecular weights of the silicone fluid is preferably in the range of from 2,000 to 500,000.

Silicone fluid (ii) can also be a mixture of two or more silicone fluids of different viscosities. For example, silicone fluid (ii) can be a mixture of two or more low viscosity silicone fluids (e.g., 100 cSt-500 cSt), two or more high viscosity silicone fluids (e.g., 1,000-20,000 cSt), or one or more low viscosity silicone fluids in combination with one or more high viscosity silicone fluids.

Particulate metal oxide (iii) can be any of the suitable metal oxides known in the art. Some examples of suitable metal oxides include fumed, precipitated or plasmatic forms of titania, alumina, silica, alumina-silica, zironia, zirconia-silica and any combinations thereof.

A particularly preferred particulate metal oxide (iii) is silica. The particulate silica can be any suitable form thereof including fumed and precipitated forms of silica. Combinations of fumed and precipitated forms of silica are also contemplated.

Particulate metal oxide (iii), and particularly silica, can be hydrophilic when combined with the other components of the reequilibration reaction mixture. Alternatively, at least a part of particulate metal oxide (iii) can be pre-hydrophobized (to provide mixture (3) herein) using a suitably hydrophobic organosilane or alkyl-containing silicone fluid before being combined with branched silicone resin (i) and silicone fluid (ii). For example, particulate metal oxide (iii) can be pre-hydrophobized by reaction with a hydrophobic silane compound (e.g., $(CH_3)_3SiOH$, $(CH_3)_3SiCl$ or hexamethyldisilazane) prior to mixing with branched silicone resin (i) and silicone fluid (ii).

Particulate metal oxide (iii) can also include a mixture of pre-hydrophobized and non-prehydrophobized (i.e., hydrophilic) forms of the selected metal oxide. In such mixtures, the weight ratio of pre-hydrophobized to non-prehydrophobized silicas is preferably in the range of from 1:20 to 20:1. For example, in different embodiments, the weight ratio of pre-hydrophobized to non-prehydrophobized silicas can be 1:20, 1:10, 1:5, 1:4, 1:3, 1:2, 1:1, 2:1, 3:1, 4:1, 5:1, 10:1 or 20:1.

In addition, the hydrophobized portion of particulate metal oxide (iii) need not be completely surface-coated with hydrophobizing agent. For example, the hydrophobized metal oxide can be partially hydrophobized, e.g., 95%, 90%, 80%, 70% or 50% of its surface may be hydrophobized.

Suitable hydrophobized forms of silica are commercially available. Particularly preferred forms of hydrophobized silica are commercially available under the Sipernat® and Aerosil® trade names (Evonik Industries).

Particulate metal oxide (iii) can have any suitable particle size. For example, the metal oxide can have a particle size of from 5 nanometers up to several hundred microns. More preferably, the metal oxide has an average particle size in the range of from 1 to 20 microns. Surface area of particulate metal oxide (iii) is preferably within the range of from 50 to 1000 square meters per gram ($m^2/g$). For example, the metal oxide can be selected to have a surface area in the range of from 50 to 500, or 60 to 450, or 80 to 400 $m^2/g$.

The amount of particulate metal oxide (iii) is preferably not greater than 20% by weight of reequilibration reaction mixture. For silicas, amounts of up to 20% are suitable with amounts ranging from 1 to 10% by weight of the reequilibration reaction mixture being preferred. In one embodiment, fumed silica is present in an amount not greater than 6% by weight and precipitated silica in an amount not greater than 15% by weight of the reequilibration reaction mixture.

As stated above, part or all of antifoam component (c) can be provided as the equilibration reaction product of aforedescribed mixture (1), i.e., as antifoam mixture (2). Equilibration of mixture (1) to provide antifoam mixture (2) can be achieved by subjecting mixture (1) to suitable equilibration reaction conditions, e.g., heating to a temperature of from 20 to 200 and preferably from 150 to 180, ° C., preferably under agitation and preferably in the presence of a catalytically effective amount of at least one catalyst (iv) for catalyzing the condensation of siloxy groups.

Some examples of useful optional catalysts (iv) include alkali metal hydroxides (e.g., potassium hydroxide, sodium hydroxide and cesium hydroxide), alkali metal silanolates (e.g., potassium silanolate), alkali metal alkoxides (e.g., potassium ethoxide), quaternary ammonium hydroxides (e.g., betahydroxyethyltrimethyl ammonium hydroxide, benzyltrimethyl ammonium hydroxide, tetramethyl ammonium hydroxide), quaternary ammonium silanolates, quaternary phosphonium hydroxides, and metal salts of organic acids (e.g., dibutyltin laurate, stannous acetate, stannous octanoate, and the like).

In general, antifoam component (c) can be incorporated in the adjuvant composition herein at a level of from 0.0001 to 1.0, and preferably at from 0.001 to 0.5, weight percent thereof. In antifoam component (c), branched silicone resin (i) can be present, e.g., at from 1 to 35, and preferably from 2 to 20, weight percent, silicone fluid (ii) can be present, e.g., at from 50 to 99, and preferably from 70 to 98, weight percent, particulate metal oxide (iii) can be present, e.g., at from 0.1 to 15, and preferably from 0.1 to 10, weight percent, and optional catalyst (iv) is present in at least a catalytically effective amount, e.g., from 0.01 to 5, and preferably from 0.1 to 1, weight percent.

Water (e)

The amount of water (e) present in the adjuvant composition of this invention can vary from the minimum required for substantially complete dissolution of water-soluble electrolyte (a) and any other water-soluble materials contained therein, e.g., on the order of from 30 to 95, and preferably from 40 to 90, weight percent of the total water-solubles, in which case the adjuvant composition can be considered a concentrate, up to the full amount of water required for the application-ready agrochemical formulation prepared therewith, e.g., a dilution ratio of water (d) to the total weight of ingredients (a), (b), (c) and optional ingredient(s) (e) of from 1:1 to 100:1, and more commonly from 10:1 to 50:1.

Agrochemical (f)

Agrochemical (f) in the agrochemical formulation of this invention includes, without limitation, bioactive compounds, biological materials including extracts, fractions and by-products thereof, living organisms, and the like, that function as pesticides, herbicides, fungicides, insecticides, nematocides, larvacides, mitocides, ovacides, plant growth regulators, seed treatment agents, etc. Agrochemical (f) is preferably water-soluble, water-dispersible or soluble in water-organic solvent mixtures. Suitable agrochemicals (f) are known to those skilled in the art and are listed in standard reference works such as the Pesticide Manual (British Crop Protection Council). The agrochemical formulation herein contemplates known and conventional levels of agrochemical (s) (f) therein.

Typical uses for pesticides include agricultural, horticultural, turf, ornamental, home and garden, veterinary and forestry applications.

The term "pesticide" refers to any substance used to destroy pests, e.g., rodenticides, insecticides, miticides, fungicides, and herbicides. Illustrative examples of pesticides which can be incorporated in the agricultural formulation herein include, but are not limited to, growth regulators, photosynthesis inhibitors, pigment inhibitors, mitotic disrupters, lipid biosynthesis inhibitors, cell wall inhibitors, cell membrane disrupters and infectious microorganisms. The amount of pesticide employed will, of course, vary with its type. Known and conventional levels of pesticides(s) are contemplated.

The pesticide can be a liquid or solid and be water soluble or of essentially no or low solubility in water in which case it is preferable that it be solubilized prior to incorporation in the adjuvant composition of the invention. One or more components of the adjuvant composition, e.g., electrolyte-tolerant surfactant(s) (b) and/or solvent(s) (d), may function as solubilizing agents for this purpose.

Specific examples of pesticide compounds that can be used herein as agrochemical (f) include, but are not limited to, herbicides and growth regulators such as: phenoxy acetic acids, phenoxy propionic acids, phenoxy butyric acids, benzoic acids, triazines and s-triazines, substituted ureas, uracils, pyridate, amitrole, clomazone, fluridone, norflurazone, dinitroanilines, isopropalin, oryzalin, pendimethalin, prodiamine, trifluralin, glyphosate, glufosinate, imazapyr, imazethapry, dicamba, fomesafen, 2,4-dichlorophenoxyacetic acid, sulfonylureas, imidazolinones, clethodim, diclofopmethyl, fenoxaprop-ethyl, sethoxydim, dichiobenil, isoxaben, and bipyridylium compounds. Fungicide compositions that can be used with the compounds of the present invention include, but are not limited to, aldimorph, tridemorph, dodemorph, dimethomorph, flusilazol, azaconazole, cyproconazole, epoxiconazole, furconazole, propiconazole, tebuconazole, imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, dodicin and dodine.

Insecticide, larvacide, miticide and ovacide compounds that can be used with the adjuvant composition of the present invention include, but are not limited to, *Bacillus thuringiensis* (Bt), spinosad, abamectin, doramectin, lepimectin, pyrethrins, amitraz, boric acid, imidacloprid, diazinon, kelevan, izoxathion, chlorpyrifos, clofentezine, lambda-cyhalothrin, permethrin, bifenthrin, cypermethrin, and the like.

Of the foregoing compounds, the water-soluble herbicides are particularly advantageous for incorporation in the agrochemical formulation of this invention with glyphosate, glufosinate, imazapyr, imazethapyr, dicamba, fomesafen and 2,4-dichlorophenoxyacetic acid being preferred. It shall be understood herein that these preferred herbicides include all of their salts and other forms, numerous ones of which are known in the art.

The following examples are illustrative of the adjuvant composition and agrochemical formulation of the invention.

Example 1

Comparative Examples 1 and 2

The foam control characteristics of a base adjuvant composition containing an antifoam component A in accordance with the invention (Example 1) were compared with those of the base adjuvant composition containing known antifoam components B (Comparative Example 1) and C (Comparative Example 2). The base adjuvant composition was prepared by solubilizing 35 percent by weight of ammonium sulfate as water-soluble electrolyte (a) and 10 percent by weight of alkylpolyglucoside Agnique PG 8107 as electrolyte-tolerant surfactant (b) in 55 percent by weight of water (e). To this base adjuvant composition were individually added antifoam components A, B and C in the levels of concentration indicated in Table 1, infra.

Antifoam component A, which is representative of antifoam component (c) of the invention, was obtained as the equilibration reaction product of the following mixture:

| Equilibration Reaction Mixture Component | Amount (parts by wt.) |
|---|---|
| branched silicone resin (i): | |
| $M_{0.6}Q$ | 14.7 |
| silicone fluid (ii): | |
| L-45/350 of Momentive Performance Materials Inc. (dimethyl silicone oil of 350 cSt at 25° C. | 82.0 |
| particulate metal oxide (iii): | |
| Aerosil R-812 silica (Evonik) | 3.0 |
| Catalyst (iv): | |
| KOH | 0.3 |
| Water | 0.5 |

Equilibration of the foregoing mixture absent its water component was carried out by heating at 150-200° C. for 1 day under continuous stirring. To the equilibration reaction product at ambient temperature was added the indicated amount of water.

Antifoam component B has the following composition: 96.0 percent by weight of dimethyl silicone oil (500 cSt at 25° C.), 3.0 percent by weight of silica and 1.0 percent by weight of potassium silanolate-terminated polydimethylsiloxane. Antifoam component C is a 10% emulsion of antifoam component B.

The level of foam control was determined by the following test:

Foam Test

A 4 ounce (110 ml) glass jar is filled with 60 grams of adjuvant composition. The jar is then shaken in a mechanical shaker for a predetermined amount of time. When the shaker stops, the time required for the resulting head of foam to collapse is recorded. As the height of foam decreases, it passes through an upper, and then a lower, light detector. The light detectors are placed approximately 17 mm apart. The defoam rate (lower detector time−upper detector time) is then calculated. The lower the defoam rate, the better the defoam properties of the adjuvant composition.

In the foam control tests whose results are presented below in Table 1, the adjuvant compositions containing antifoam components A, B and C were shaken for 5 seconds and then held still for 2 minutes while the defoam rate was determined. The composition were then shaken for 1 minute and held still for 2 minutes while the defoam rate was determined. This process was repeated to determine the defoam rate after 2 minutes, 5 minutes, 10 minutes and 15 minutes of shaking. This repeated shaking allows the persistence of each antifoam component to be determined.

The results of the foam control tests obtained with each of antifoam components A, B and C, expressed as defoam rate versus antifoam concentration, are set forth below in Table 1:

TABLE 1

Foam Control vs. Antifoam Concentration Employing Antifoam Components A, B and C

| Antifoam A Concentration (ppm) | 1 min Defoam Rate* (sec) | 2 min Defoam Rate (sec) | 5 min Defoam Rate (sec) | 10 min Defoam Rate (sec) | 15 min Defoam Rate (sec) |
|---|---|---|---|---|---|
| 1000 | 2 | 1.5 | 2 | 2.5 | 3 |
| 500 | 0.5 | 0 | 0 | 0.5 | 0.5 |
| 250 | 1 | 1 | 1.5 | 2 | 2 |
| 125 | 3 | 3.5 | 4 | 5.5 | 8.5 |
| 120 | 4 | 2.5 | 4 | 4 | 5.5 |
| 120 | 11 | 13 | 17.5 | 12.5 | 15 |
| 100 | 3.5 | 3 | 5 | 4.5 | 4.5 |
| 62.5 | 2.5 | 3.5 | 4 | 5.5 | 8.5 |
| 60 | 7 | 5.5 | 6 | 6 | 8.5 |
| 50 | 25 | 25 | 29 | 38 | 28 |
| 50 | 10.5 | 14.5 | 20.5 | 17 | 19 |
| 30 | 8.5 | 11.5 | 13 | 15 | 17.5 |
| 15 | 12.5 | 8 | 23.5 | 24.5 | 19.5 |
| 7.5 | 7 | 11 | 14 | 14 | 16 |
| 3.75 | 9 | 14.5 | 28.5 | 30.5 | 24 |

| | 1 min Defoam Rate (sec) | 2 min Defoam Rate (sec) | 5 min Defoam Rate (sec) | 10 min Defoam Rate (sec) | 15 min Defoam Rate (sec) |
|---|---|---|---|---|---|
| Antifoam B Concentration (ppm) | | | | | |
| 2000 | 1.5 | 0.5 | 0.5 | 2.5 | 11 |
| 1000 | 0 | 0 | 0 | 4 | 20 |
| 500 | 1.5 | 0.5 | 2.5 | 31 | 61 |
| 250 | 8 | 13 | 22 | 61.5 | 80.5 |
| 125 | 18.5 | 48 | 91 | 120 | 120 |
| Antifoam C Concentration (ppm) | | | | | |
| 10.000 | 120 | 120 | 120 | 120 | 120 |
| 1000 | 120 | 120 | 120 | 120 | 120 |

The data in Table 1 and FIG. 1 show how much more effective antifoam A is at controlling the foam in the base adjuvant composition than traditional PDMS/silica based antifoams like antifoams B and C. It will be readily appreciated from FIG. 1 that antifoam component A provides the same level of foam control as 10-100 times the concentration of antifoam component B. Antifoam component C, an industry standard, failed to control foam produced by the base adjuvant composition even at the very high concentration of 1 weight percent. In addition, there significant phase separation was observed with antifoam component C.

Example 2

This example compares the long-term foam control characteristics of antifoam A in the base adjuvant composition over a period of 235 days.

FIG. 2 shows the excellent long-term effectiveness of antifoam A in the base adjuvant composition. The data curves of FIG. 2 show that there is little, if any, performance decline over the 235 test period. This long term performance is a strong indicator of the excellent stability of antifoam A in high electrolyte content adjuvant compositions. If the adjuvant composition was not stable, antifoam A would rise to the surface in this dense liquid and no longer provide foam control properties since the samples for foam testing are taken from the middle of the storage container.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. An adjuvant composition comprising:
   (a) at least one water-soluble electrolyte;
   (b) at least one electrolyte-tolerant surfactant;
   (c) antifoam component which is at least one mixture selected from the group consisting of
      (1) at least one branched silicone resin (i) of the general formula $M_a T_b D_a Q_d$ wherein M is $SiO_{1/2}(R^1)_3$, T is $SiO_{3/2}R^2$, D is $SiO_{2/2}(R^3)_e$, Q is $SiO_{4/2}$, $R^1$, $R^2$ and $R^3$ each independently is a monovalent hydrocarbon radical of from 1 to 18 carbon atoms, a is >0.1, b is 0 to 1000, C is 0 to 1,000 and d is 1-1000, at least one silicone fluid (ii) which is a polydimethylsiloxane-containing polymer, at least one particulate metal oxide (iii) which is at least one member selected from the group consisting of fumed, precipitated or plasmatic forms of titania, alumina, silica, alumina-silica, zirconia, zirconia-silica and pre-hydrophobized forms thereof and, optionally, at least one catalyst (iv) for catalyzing the condensation of siloxy groups,
      (2) the equilibration reaction product of mixture (1), and
      (3) mixture (1) in which at least a portion of particulate metal oxide (iii) is pre-hydrophobized;
   (d) optionally, at least one additional bioinert material; and,
   (e) water,
   wherein: (a) water-soluble electrolyte (a) is present at from 5 to 60 weight percent; (b) electrolyte-tolerant surfactant (b) is present at from 1 to 30 weight percent; and, (c) antifoam component (c) is present at from 0.0001 to 1.0 weight percent, and in antifoam component (c), branched silicone resin (i) is present at from 1 to 35 weight percent, silicone fluid (ii) is present at from 50 to 99 weight percent and particulate metal oxide (iii) is present at from 0.1 to 15 weight percent.

2. The adjuvant composition of claim 1 wherein:
   (a) water-soluble electrolyte (a) is at least one member selected from the group consisting of ammonium sulfate, ammonium nitrate, ammonium phosphate, urea ammonium nitrate and calcium chloride; and,
   (b) electrolyte-tolerant surfactant (b) is at least one member selected from the group consisting of alkyl polyglucosides, ethoxylated alkylamines, betaines, N-acyl sarcosinates, N-acyl glutamates, alkyl phosphates, alkylether phosphates and quaternary ammonium surfactants.

3. The adjuvant composition of claim 2 wherein: (c) in antifoam component (c), branched silicone resin (i) is an MQ resin having an M:Q ratio of from 0.1:1 to 1.5:1, silicone fluid (ii) is a polydimethyl silicone fluid and particulate metal oxide (iii) is particulate silica.

4. The adjuvant composition of claim 1 including bioinert material (d), bioinert material (d) being at least one member selected from the group consisting of solvent, wetting agent, dispersant, emulsifier, penetrant, preservative, antifreeze agent, evaporation inhibitor, colorant, pH modifier, buffering agent, thixotropic agent and viscosity modifier.

5. The adjuvant composition of claim 1 wherein:
   (a) water-soluble electrolyte (a) is present at from 10 to 50 weight percent;
   (b) electrolyte-tolerant, high foaming surfactant (b) is present at from 1 to 20 weight percent; and,
   (c) antifoam component (c) is present at from 0.001 to 0.5 weight percent, and in antifoam component (c), branched silicone resin (i) is present at from 5 to 25 weight percent, silicone fluid (ii) is present at from 65 to 94 weight percent and particulate metal oxide (iii) is present at from 1 to 10 weight percent.

6. The adjuvant composition of claim 2 wherein:
   (a) water-soluble electrolyte (a) is present at from 10 to 50 weight percent;
   (b) electrolyte-tolerant, high foaming surfactant (b) is present at from 1 to 20 weight percent; and,
   (c) antifoam component (c) is present at from 0.001 to 0.5 weight percent, and in antifoam component (c), branched silicone resin (i) is present at from 5 to 25 weight percent, silicone fluid is present at from 65-94 weight percent and particulate metal oxide (iii) is present at from 1 to 10 weight percent.

7. The adjuvant composition of claim 3 wherein:
   (a) water-soluble electrolyte (a) is present at from 10 to 50 weight percent;
   (b) electrolyte-tolerant, high foaming surfactant (b) is present at from 1 to 20 weight percent; and,
   (c) antifoam component (c) is present at from 0.001 to 0.5 weight percent, and in antifoam component (c), branched silicone resin (i) is present at from 5 to 25 weight percent, silicone fluid (ii) is present at from 65 to 94 weight percent and particulate metal oxide (iii) is present at from 1 to 10 weight percent.

8. An agricultural formulation comprising the adjuvant composition of claim 1 and (f) at least one agrochemical.

9. The agricultural formulation of claim 8 wherein agrochemical (f) is a water-soluble herbicide.

10. The agricultural formulation of claim 8 wherein agrochemical (f) is at least one member selected from the group consisting of glyphosate, glufosinate, imazapyr, imazethapyr, dicamba, fomesafen and 2,4-dichlorophenoxyacetic acid.

11. An agricultural formulation comprising the adjuvant composition of claim 2 and (f) at least one agrochemical.

12. The agricultural formulation of claim 11 wherein agrochemical (f) is a water-soluble herbicide.

13. The agricultural formulation of claim 11 wherein agrochemical (0 is at least one member selected from the group consisting of glyphosate, glufosinate, imazapyr, imazethapyr, dicamba, fomesafen and 2,4-dichlorophenoxyacetic acid.

14. The adjuvant composition of claim 1 wherein the silicone fluid (ii) comprises a mixture of at least two silicone fluids of different viscosities.

15. The adjuvant composition of claim 1 wherein the metal oxide is pre-hydrophobized.

16. The adjuvant composition of claim 1 comprising a catalyst selected from the group consisting of alkali metal hydroxides, alkali metal silanolates, alkali metal alkoxides, quaternary ammonium hydroxides, quaternary ammonium silanolates, quaternary phosphonium hydroxides, and metal salts of organic acids.

17. The adjuvant composition of claim 1 comprising a catalyst selected from the group consisting of potassium hydroxide, sodium hydroxide, cesium hydroxide, potassium silanolate, potassium ethoxide, betahydroxyethyltrimethyl ammonium hydroxide, benzyltrimethyl ammonium hydroxide, tetramethyl ammonium hydroxide, dibutyltin laurate, stannous acetate and stannous octanoate.

18. The adjuvant composition of claim 1 wherein the surfactant is alkylpolyglucoside.

\* \* \* \* \*